United States Patent [19]

Vargo

[11] Patent Number: 4,938,207
[45] Date of Patent: Jul. 3, 1990

[54] KNEE BRACE HAVING PLURALITY OF FLUID FILLED CHAMBERS SURROUNDING KNEE

[75] Inventor: Alexander C. Vargo, 17617 Midway Rd., #209, Dallas, Tex. 75252

[73] Assignee: Alexander C. Vargo, Dallas, Tex.

[21] Appl. No.: 920,411

[22] Filed: Oct. 20, 1986

[51] Int. Cl.⁵ .............................................. A61F 5/00
[52] U.S. Cl. ........................... 128/80 C; 128/DIG. 20
[58] Field of Search ................. 120/80 C, 80 F, 80 R, 120/87 R, DIG. 20

[56] References Cited

U.S. PATENT DOCUMENTS

| | | | |
|---|---|---|---|
| 891,181 | 6/1908 | Mitchell | 128/87 R |
| 2,144,641 | 1/1939 | Snyder | 128/80 C |
| 2,884,646 | 5/1959 | Alber | 128/DIG. 20 |
| 3,318,305 | 5/1967 | Schultz | 128/80 R |
| 3,513,836 | 5/1970 | Sausse | 128/64 |
| 3,817,244 | 6/1974 | Taylor | 128/80 C |
| 3,868,952 | 3/1975 | Hatton | 128/DIG. 20 |
| 3,965,486 | 6/1976 | Lightbody | 128/165 |
| 4,116,236 | 9/1978 | Albert | 128/80 C |
| 4,201,203 | 5/1980 | Applegate | 128/80 C |
| 4,219,892 | 9/1980 | Rigdon | 128/DIG. 20 |
| 4,287,885 | 9/1981 | Applegate | 128/80 C |
| 4,323,059 | 4/1982 | Rambert et al. | 128/80 C |
| 4,445,505 | 5/1984 | Labour et al. | 128/80 C |
| 4,509,750 | 4/1985 | Last | 128/DIG. 20 |

FOREIGN PATENT DOCUMENTS

| | | | |
|---|---|---|---|
| 2737734 | 12/1970 | Fed. Rep. of Germany | 128/80 R |
| 3607003 | 10/1986 | Fed. Rep. of Germany | 128/80 C |
| 2506603 | 12/1982 | France | 128/80 R |

Primary Examiner—Edgar S. Burr
Assistant Examiner—Tonya Lamb

[57] ABSTRACT

The present invention relates to an improved knee brace having a plurality of interconnected fluid filled chambers positioned to provide variable support to the knee joint as the knee is bent. In particular, the present invention contemplates a knee brace wherein increased support is given to the side of the knee joint as the knee is bent.

8 Claims, 5 Drawing Sheets

FIG. 5
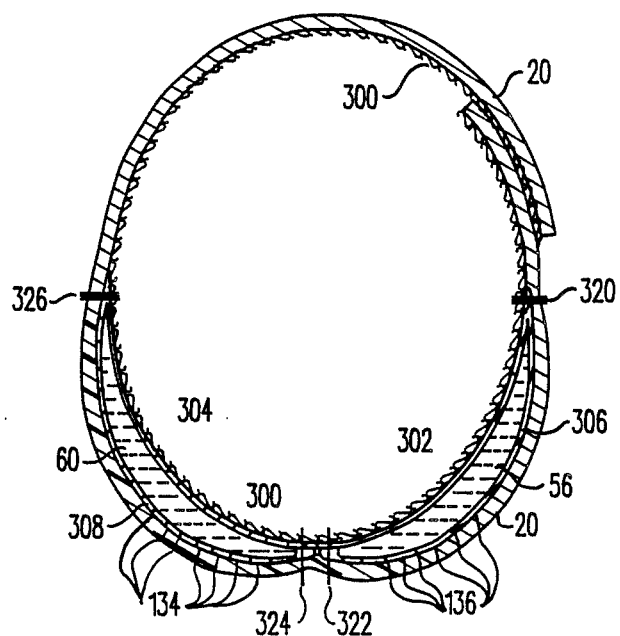
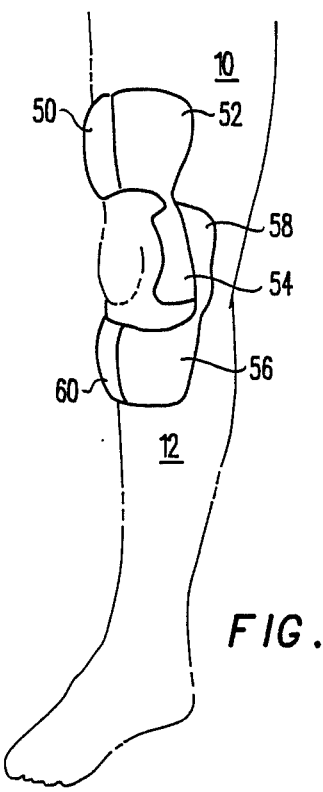
FIG. 6a
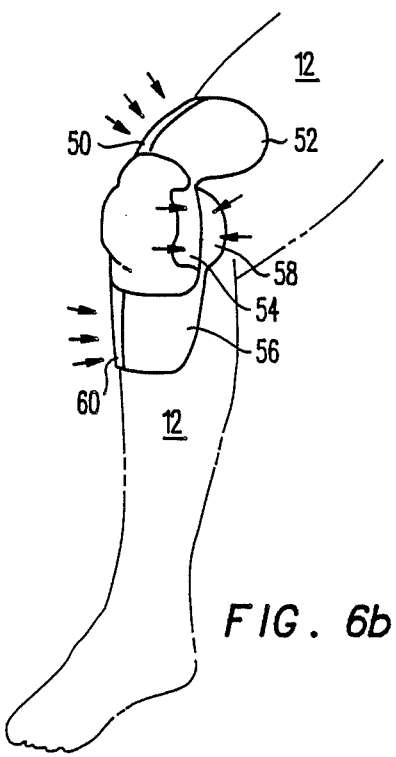
FIG. 6b

KNEE BRACE HAVING PLURALITY OF FLUID FILLED CHAMBERS SURROUNDING KNEE

TECHNICAL FIELD

The present invention relates to a knee brace having a plurality of interconnected fluid filled compartments positioned to provide variable support to the knee joint as the knee is bent.

BACKGROUND ART

It is well known in the prior art to use an apparatus which frictionally engages a human thigh and calf to prohibit abnormal lateral, fore and aft motion of these body members, avoiding improper stresses on the knee. In particular, U.S. Pat. No. 2,144,641, to Snyder, provides a knee brace which frictionally engages both the thigh and calf and has a pair of flattened vertical support shafts journaled by a rivet, where the shafts prohibit abnormal lateral, fore and aft motion of the knee. These devices are useful where the user's knee has been previously injured, protecting the knee from further injury and permitting continued activity while the knee joint is healing.

The prior art also contemplates the use of knee pads to both protect the knee and give support to it, giving greater support when the knee is bent. In particular, U.S. Pat. No. 3,965,486, to Lightbody, discloses a pneumatic knee pad having two chambers and a multiplicity of hollow fingers communicating with the chambers. When the knee is bent, the air in one or both of the chambers is forced into one or more of the fingers which tighten against the knee prohibiting separation of the various bones of the knee and reducing the risk of torn ligaments, tendons, and cartilage.

The prior art also discloses a pair of fluid filled chambers positioned on the thigh and calf adjacent the knee joint and fluidly connected so as to permit fluid migration from one side of the device to the other upon application of an external force to the knee. These devices are principally used to protect the user's knee from injuries during athletic contests while permitting free use of the leg. Upon the application of an external force, such as contact during an athletic competition, a lateral force to the knee causes fluid to migrate from the engaged side of the knee to the opposite side causing expansion of the fluid filled chamber on the opposite side. By increasing fluid pressure on the side opposite that of impact, the knee is better braced, thereby reducing the possibility of injury to the knee joint.

Although these prior art devices provide some support to the knee joint, they have failed to provide control support in conjunction with and as a result of flexure of the knee. Further, the devices have failed to provide adequate support to the knee joint without resulting in overly restricting movement of the knee. Thus, a need exists for a knee brace which provides controlled lateral support at defined points of knee flexure without restricting movement of the knee joint.

SUMMARY OF THE INVENTION

The present invention provides a knee brace having a plurality of fluid filled chambers located on the thigh and calf proximate the knee cap and fluidly connected to a plurality of side chambers mounted behind the knee cap on the side of the knee. In use, flexing the knee causes an increase in pressure in the side chambers, giving lateral support to the knee, holding a weak joint together and protecting a damaged area from further injury. Further, during walking or running, the knee will experience beneficial therapeutic effect from the pulsation of pressure in the side chambers.

In another aspect of the invention, the knee brace provides fluid chambers formed with an outer surface of an inelastic material which prohibits dissipation of hydrostatic pressure through the expansion of the outer surface, thereby concentrating the pressure on the user's knee.

According to a further aspect of the invention, the knee brace includes a plurality of fluid filled chambers located on the thigh and calf proximate the knee cap which may be either filled with or drained of fluid so as to provide application of different hydrostatic pressures to different points on the user's knee, and also to provide a means for varying the amount of hydrostatic pressure obtained when the knee is bent. This aspect of the present invention is useful in that the hydrostatic pressure may be relieved as the knee heals, or increased if the knee is re-injured to achieve the maximum therapeutic effect of the device.

BRIEF DESCRIPTION OF THE DRAWINGS

A more complete understanding of the invention and its advantages will be apparent from the following Detailed Description, taken in conjunction with the accompanying drawings in which:

FIG. 5 is a sectional view of the apparatus of the present invention taken along lines 5—5 in FIG. 2;

FIG. 6a is a perspective schematic view of the fluid compartments of the apparatus of the present invention;

FIG. 6b is a perspective schematic view of the fluid compartments of the apparatus of the present invention.

DETAILED DESCRIPTION

Figures 1, 7:
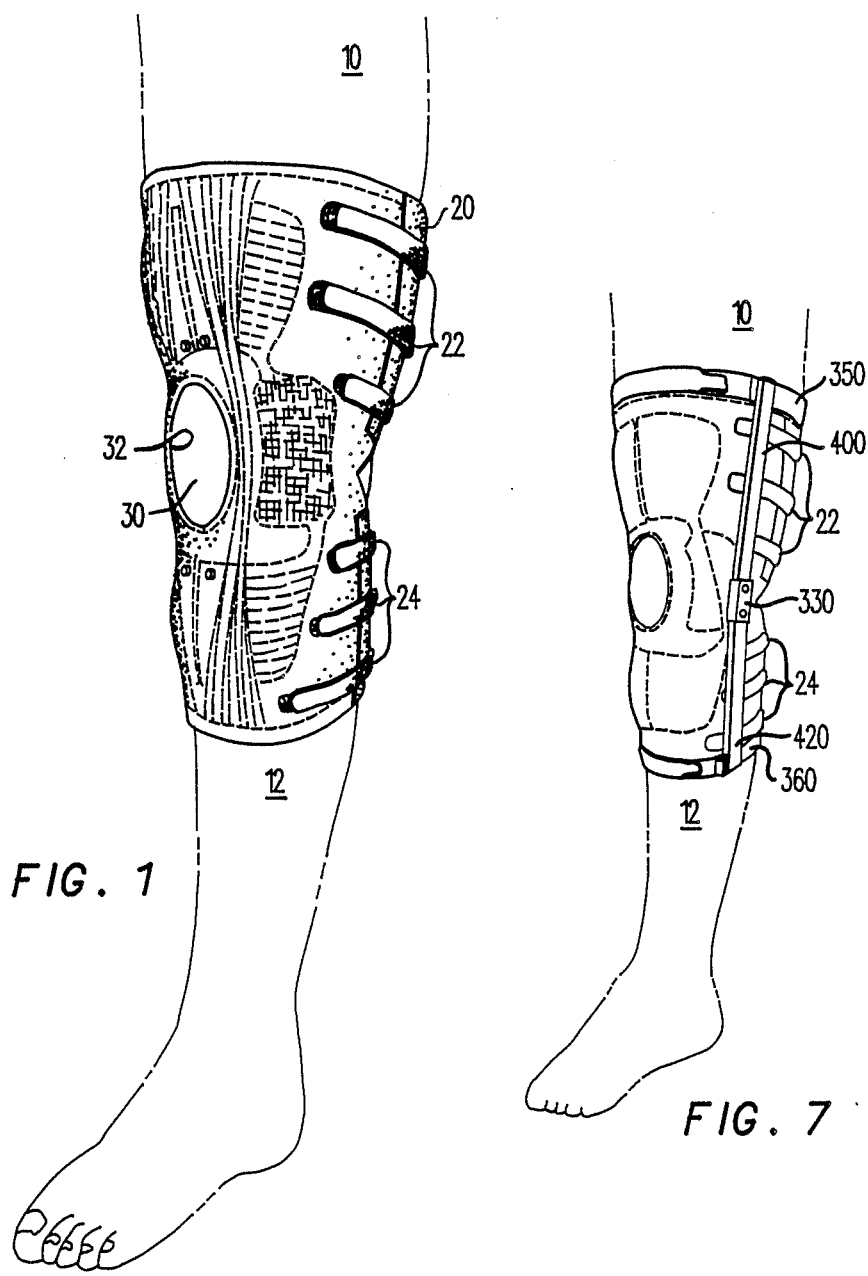
FIG. 1 is a perspective view of the apparatus of the present invention shown applied to a user's leg.
FIG. 7 is a perspective view of an alternative embodiment of the apparatus of the present invention.
Figure 2:
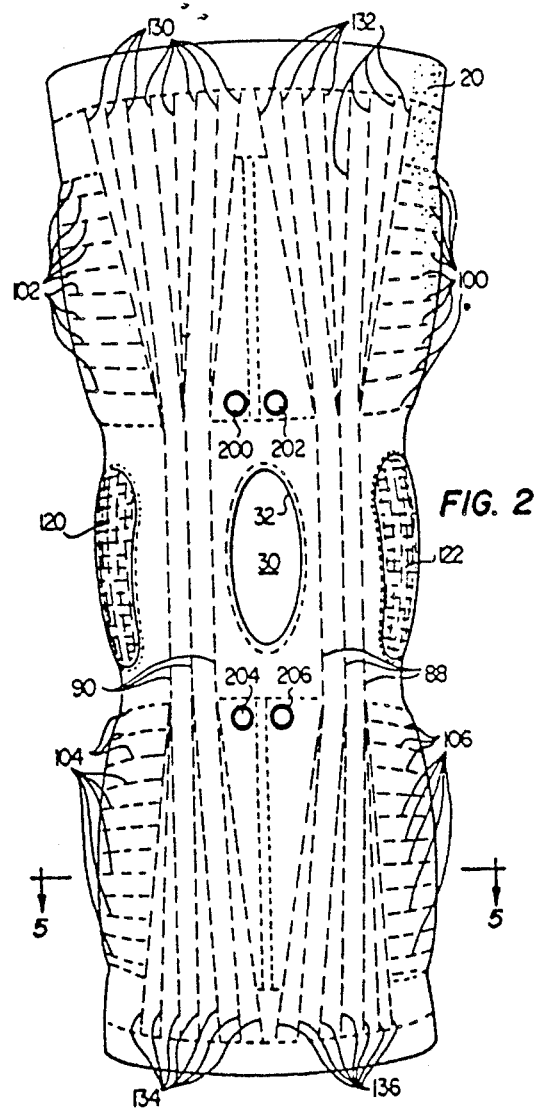
FIG. 2 is a front view of the apparatus of the present invention.
Figure 3:
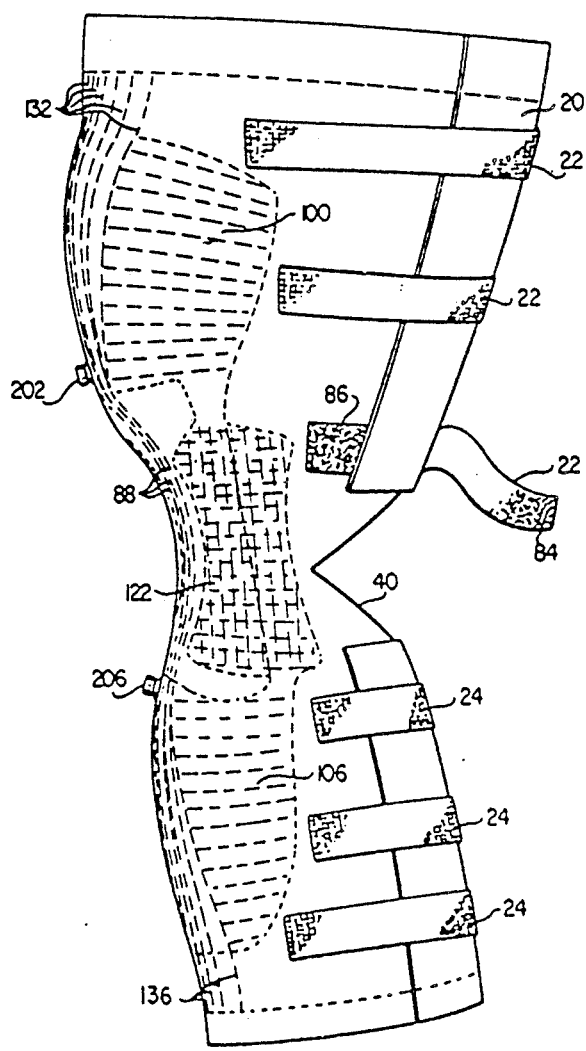
FIG. 3 is a side view of the apparatus of the present invention.

Referring initially to FIGS. 1, 2 and 3, the apparatus of the present invention comprises a flexible sheath 20 which is mounted on a human thigh 10 and calf 12 so as to frictionally engage the leg at the knee area. Sheath 20 is made of a flexible material such as cloth or neoprene, but is of sufficient strenght to allow it to be securely mounted about the leg while simultaneously allowing the leg to bend at the knee. Sheath 20 has an ovular cutout 30 defined by edge 32, and is located so as to receive the patella, commonly known as the knee cap, allowing the patella to protrude from sheath 20 to permit greater flexibility of the knee. Further, cutout 30 is sized so as to retain and locate the patella to eliminate the risk of improper movement of the patella due to broken or injured tendons.

The apparatus of the present invention is secured about the user's leg above the knee by adjustable straps 22 and below the knee by adjustable straps 24. It will be understood that straps 22 and 24 can employ VELCRO (hook and loop) fastening surfaces to allow precise adjustment of the fit of sheath 20, and that in alternative embodiments, buttons, snaps, hooks or zippers, for example, may be employed if suitable. As shown in FIG. 3, straps 22 have VELCRO fastening surfaces 84 located so as to engage with cooperating VELCRO attachment surfaces 86 located on sheath 20 to provide a secure fit of the sheath above the user's thigh. Further, while FIGS. 1, 2 and 3 show three straps above the knee and three straps below the knee, more or fewer straps may be employed as deemed suitable. For example, if the apparatus of the present invention is to be worn during athletic competition more staps may be employed to assure that the apparatus does not slip during use.

Figure 4:
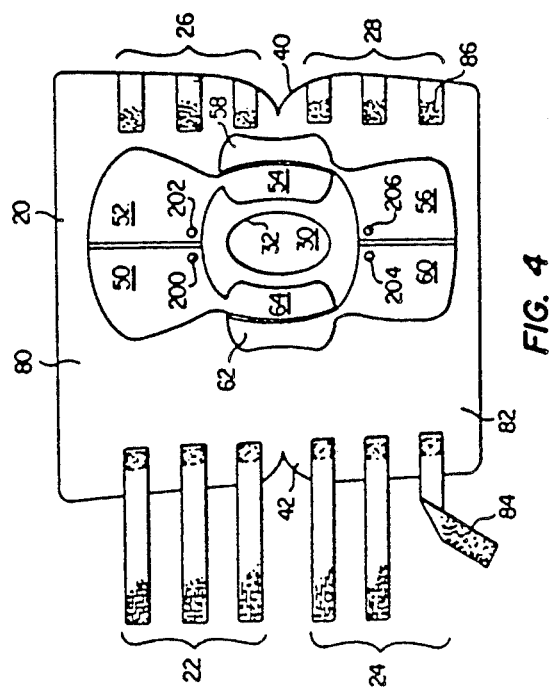
FIG. 4 is a top view of the apparatus of the present invention shown in a flat position.

Referring now to FIG. 4, sheath 20 is shown in a flat position. Proximate to ovular cutout 30 are fluid chambers 50 and 52, which during use are located above the knee cap, and fluid chambers 56 and 60, which during use are located below the knee cap. Fluidly connected to each of these chambers is a corresponding side chamber, which during use are located to the side and behind the knee cap. In particular, fluid chamber 50 is fluidly connected to side chamber 64, chamber 52 is connected to side chamber 54, chamber 56 is connected to side chamber 58 and chamber 60 is connected to side chamber 62.

As shown in FIG. 4, sheath 20 has cutouts 40 and 42. Proximate cutout 42 are flaps 80 and 82 on which straps 22 and 24 are located. Cutouts 40 and 42 are located so that when sheath 20 is mounted on the leg, the cutouts are located directly behind the knee cap to allow the user to bend his knee freely without binding or other interference from the sheath.

As shown in FIGS. 2 and 3, inelastic fibers are employed in the exterior boundary of the fluid chambers. In particular, chamber 50 has lateral fibers 102 overlaid with vertical fibers 130 to comprise its external surface. Likewise, fluid chamber 52 has lateral fibers 100 overlaid with vertical fibers 132 to comprise its external surface. Similar fiber configurations are used for chamber 60 where lateral fibers 104 and vertical fibers 134 comprise its exterior surface, and for chamber 56 where lateral fibers 106 and vertical fibers 136 are employed. Vertical fibers 130 and 132 are connected to vertical fibers 134 and 136, respectively, by fibers 88 and 90, which fibers lie proximate to ovular cutout 30. In addition to connecting the vertical fibers above and below cutout 30, fibers 88 and 90 also serve to retain and locate the user's knee cap during use.

In the preferred embodiment, fibers 130, 132, 134, 136, 88, 90, 100, 102, 104, and 106 comprise metallic fibers interwoven with the material that comprises the outer surface of the various fluid chambers. This can be accomplished by sewing the appropriate layer or layers with wire thread. Similarly, side chambers 54 and 58 have an exterior surface comprising a tightly interwoven fiber structure. The tight weave of inelastic fibers 122 (as shown in FIG. 3) assures that little or no external deformation of chambers 54 and 58 occur, and that all expansion due to increasing pressure in these chambers is directed and focused towards the interior surfaces of these chambers proximate to the user's knee. Likewise, inelastic fibers 120 comprise a tightly interwoven fiber structure covering side chambers 62 and 64, assuring that all increases in pressure in these chambers is directed and focused towards the surface proximate to the user's knee.

It will be understood that chambers 50, 52, 54, 56, 58, 60, 62 and 64 can be filled with air, water, gelatin, or other fluids which can easily compress between the chambers above and below cutout 30 and the various side chambers. As shown in FIG. 2, valves 200, 202, 204, and 206 allow fluid or air to be injected into or removed from chambers 50, 52, 60, and 56, respectively.

Referring now to FIG. 5, sheath 20 has located on its interior surface facing 300. Facing 300 is of a suitable material, such as cloth, so as to readily frictionally engage the user's thigh and calf to comfortably secure the apparatus of the present invention about the user's knee. Chambers 56 and 60 have inner liners 302 and 304, respectively, and outer liners 306 and 308, respectively. These liners serve to retain the fluids contained in each of these chambers, and it will be understood that all of the fluid chambers of the present invention have similar liners. Inelastic fibers 134 and 136 are shown as interwoven with the material of sheath 20. The boundaries of each fluid chamber is reinforced with a strong inelastic stitching, such as wire stitching. In particular, as shown in FIG. 5 the boundaries of fluid chambers 56 are reinforced with wire stitching 320 and 322, and the boundaries of fluid chambers 60 are reinforced with wire stitching 324 and 326.

As shown in FIG. 7, the apparatus of the present invention may be used in combination with the standard knee brace as used in the prior art. In particular, the apparatus of the present invention may be used in conjunction with two pair of flattened vertical support shafts journaled by a rivet, which pair of shafts prohibit abnormal lateral, fore and aft motion of the knee. As is seen in FIG. 7, the apparatus of the present invention is used in conjunction with vertical shafts 400 and 420 that are connected by journal 330 at a point corresponding to the point at which the human knee flexes. Vertical shafts 400 and 420 are attached to support straps 350 and 360, respectively. Support strap 350 frictionally engages about the user's thigh and support strap 360 frictionally engages about the user's calf, and serve to support a corresponding pair of vertical shafts (not shown) on the side of the knee opposite to shafts 400 and 420. It will be understood that shafts 400 and 420 prohibit normal lateral, fore and aft motion of the user's knee and may be used in conjunction with the apparatus of the present invention to promote healing of prior existing injuries to the knee and to prohibit future injuries of the knee which may be occasioned during athletic competition.

In operation, the user places sheath 20 with its self-contained fluid chambers about his thigh and calf so that the knee cap protrudes through cutout 30. Adjustable straps 22 and 24 are fastened so that sheath 20 is comfortably engaged with the user's thigh and calf to permit walking and/or running activities. When the user's leg is in a straight position (as shown in FIG. 6a) the fluid pressure in each of the fluid chambers is at a minimum and is evenly distributed on the interior surface of sheath 20 at points both above and below the knee cap and to each side of the knee cap. During use, when the user bends the knee, the volumes of fluid chambers 50, 52, 56, and 60 are decreased. In particular, the inelastic fibers which span the outer surfaces of these fluid chambers are pulled tight so as to decrease their respective volumes. Consequently, the fluid pressure in each chamber increases, and the increase in pressure is distributed to the various side chambers. This increase in pressure in the side chambers is directed to the sides of the user's knee because of the inelastic outer covering 120 and 122 of these side chambers.

Prior to the mounting of sheath 20 on the user's leg, the user may insert or remove fluid from the various fluid chambers through valves 200, 202, 204, and 206. Specifically, each fluid compartment may be filled with a moderate amount of air, water, gel or other fluid so as to result in only a moderate force upon the side of the knee during operation. Further, various fluid chambers may be filled or drained so as to either increase or decrease the resulting pressure at a desired location on the side of the knee. For example, if fluid chamber 52 is filled through valve 202 so as to have an excess amount of fluid therein, side chamber 54 would exert a correspondingly higher pressure to the side of the user's knee than would the other side chambers 58, 62, and 64. Likewise, fluid chamber 52 can be drained through valve 202 so that the corresponding pressure exerted on the user's knee by side chamber 54 would be less than the pressures exerted by the other side chambers.

Thus, the present invention provides a knee brace which provides lateral support to the knee and where such support may be adjusted in accordance with the amount of fluid loaded in the respective chambers provided by the brace. Further, upon flexing of the knee, the brace provides added pressure at the sides of the knee joint thus providing additional lateral support. By adjusting the fluid pressure in the four separate chambers, the knee brace can be tailored to the specific needs of the user. Further, because four separate chambers are provided, different fluids may be selected and used in the various chambers, thus further adding to the versatility of the brace. Additionally, because of the varying pressures which result as the knee is flexed while using the present knee brace, a massaging action is provided, where desired. Additionally, heated or cooled fluids may be used to provide the therapeutic benefit which will be occasioned by the use of such fluids at the desired locations adjacent the knee joint. Further, all of these benefits are provided with a brace which is both easy to apply and which provides a minimum of restriction with respect to movement of the knee. Further, when the leg is at the extended, normally at rest position, the pressures applied by the brace are at a minimum.

Although preferred embodiments of the invention have been described in the foregoing detailed description and illustrated in the accompanying drawings, it will be understood that the invention is not limited to the embodiments disclosed, but is capable of numerous rearrangements, modifications, and substitution of parts and elements without departing from the spirit of the invention. The present invention is therefore intended to encompass such rearrangements, modifications, and substitution of parts and elements as fall within the scope of the invention.

I claim:

1. A knee brace comprising:
    a flexible sheath member sized so as to extend about the human thigh and calf to embrace the knee area of the leg, having a cutout portion to receive and locate the knee cap, means to exert a hydrostatic pressure on said knee area when said knee is bent comprising first and second fluid filled chambers located so as to be proximate to the above said knee cap, each fluidly connected to a corresponding first and second side chamber, wherein said first side chamber is located on one side of the knee and said second side chamber is located on the opposite side of the knee; and a third and fourth fluid filled chamber located so as to be proximate to and below said knee cap, each fluidly connected to a corresponding third and fourth side chamber, wherein said third side chamber is located on one side of the knee and said fourth side chamber is located on the opposite side of the knee where the hydrostatic pressure in said first, second, third and fourth side chambers is increased by a corresponding increase in the hydrostatic pressure in the first, second, third and fourth fluid filled chambers occasioned upon the bending of the knee; said first, second, third and fourth chambers having no fluid interconnection with each other.

2. The knee brace of claim 1, further comprising an attachment means comprising releasable fastening straps which are adjustably secured about said sheath so as to allow said sheath to be frictionally engaged about the knee area of the human leg.

3. The knee brace of claim 1, wherein said cutout portion is sized to allow the knee cap to protrude from said sheath, and said sheath further comprises first and second notches located so that when said sheath is attached to a human leg said first and second notches are located to form a gap in said sheath behind said knee to allow free bending movement thereof.

4. The knee brace of claim 1, wherein said first, second, third and fourth fluid filled chambers have internal and external surfaces, said internal surface being proximate the knee, and located on each chamber's external surface is at least a single ply of an inelastic fiber positioned so as to substantially prohibit the expansion of each said fluid filled chamber's external surface upon the increase in hydrostatic pressure in each chamber.

5. The knee brace of claim 4, wherein said first, second, third and fourth side chambers have internal and external surfaces, and the external surface of each side chamber comprises an interwoven inelastic fiber structure positioned so as to prohibit the expansion of the side chamber's exterior surfaces upon increase of hydrostatic pressure therein, thereby directing any increase in hydrostatic pressure to each said chamber's interior surface proximate the knee area.

6. The knee brace of claim 1, further comprising a plurality of inelastic fibers located proximate to said cutout area so as to locate and retain said knee cap when said knee is bent.

7. The knee brace of claim 1, further comprising:
    first and second shafts, wherein said first shaft has first and second ends, said first end being attached to said sheath at a point above the knee and said second end being attached to said sheath at a point below the knee, said first shaft comprising first and second members journaled by a rivet at a point corresponding to the point at which the human knee flexes so as to prohibit abnormal lateral, fore, and aft motion of the knee while allowing normal flexing thereof; and
    said second shaft has first and second ends, said first end being attached to said sheath at a point above the knee and said second end being attached to said sheath at a point below the knee, said second shaft comprising first and second members journaled by a rivet at a point corresponding to the point at which the human knee flexes so as to prohibit abnormal lateral, fore and aft motion of the knee while allowing normal flexing thereof.

8. The knee brace of claim 1, further comprising means to add or remove fluid from said first fluid filled chamber, and a means to add or remove fluid from said second fluid filled chamber, wherein said fluid filling means permits the hydrostatic pressure exerted by said first and second fluid filled chambers on said knee area to be either increased or reduced a predetermined amount.

* * * * *